United States Patent [19]
Faxon et al.

[11] Patent Number: 5,464,395
[45] Date of Patent: Nov. 7, 1995

[54] CATHETER FOR DELIVERING THERAPEUTIC AND/OR DIAGNOSTIC AGENTS TO THE TISSUE SURROUNDING A BODILY PASSAGEWAY

[76] Inventors: David P. Faxon, 2027 Ashbourne Dr., South Pasadena, Calif. 91030; Christian C. Haudenschild, 7600 Timbercrest Dr., Rockville, Md. 20855

[21] Appl. No.: 223,451

[22] Filed: Apr. 5, 1994

[51] Int. Cl.⁶ ........................ A61M 29/00
[52] U.S. Cl. ............ 604/96; 604/164; 604/264
[58] Field of Search .......... 604/96, 264, 198, 604/187, 164, 51–55, 165–169; 128/831

[56] References Cited

U.S. PATENT DOCUMENTS 4,136,695  1/1979  Dafoe ................... 128/831

Primary Examiner—John D. Yasko
Attorney, Agent, or Firm—Pandiscio & Pandiscio

[57] ABSTRACT

A catheter for delivering therapeutic and/or diagnostic agents directly into the tissue surrounding a bodily passageway. The catheter comprises at least one needle cannula able to be projected outboard of the catheter so as to deliver the desired agents to the tissue. The catheter also preferably includes one or more inflatable balloons.

16 Claims, 15 Drawing Sheets

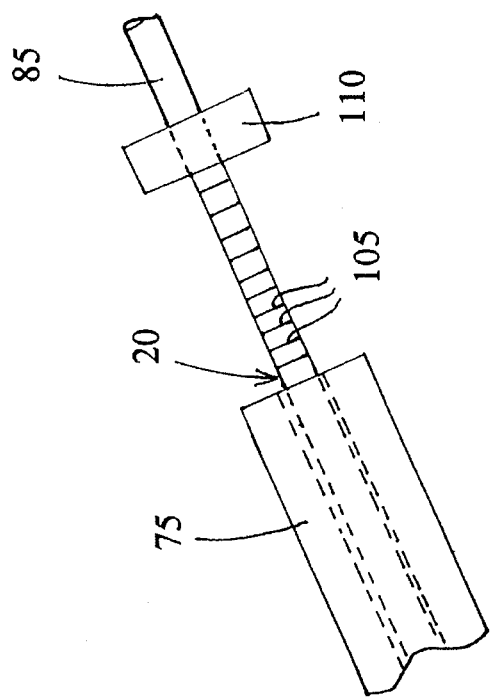
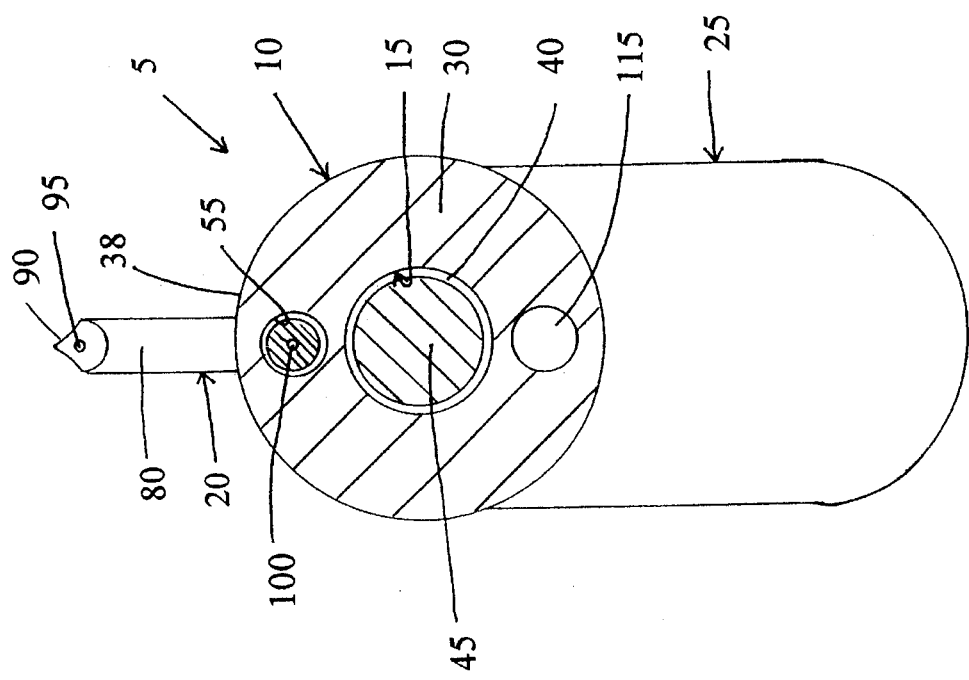

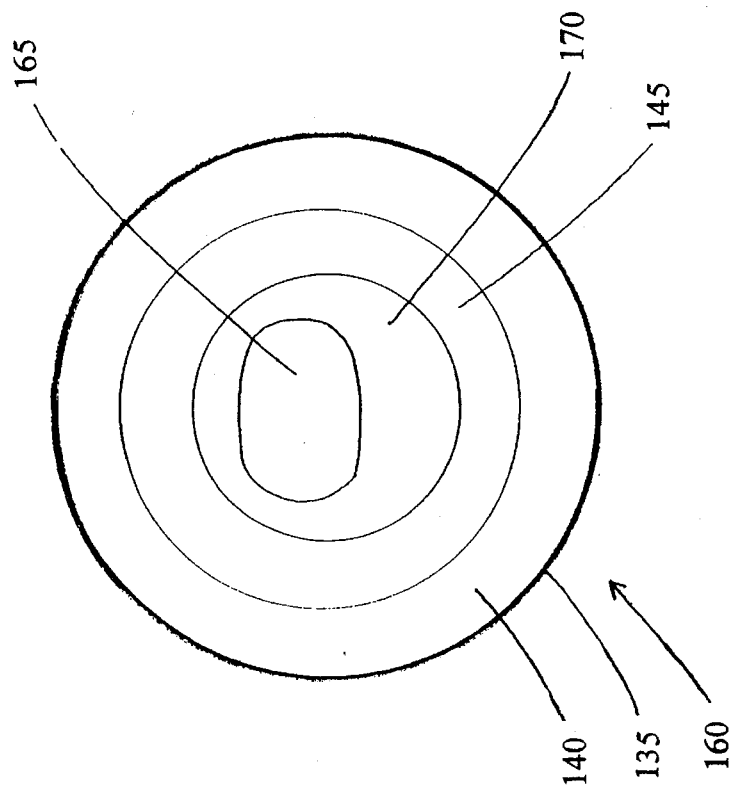
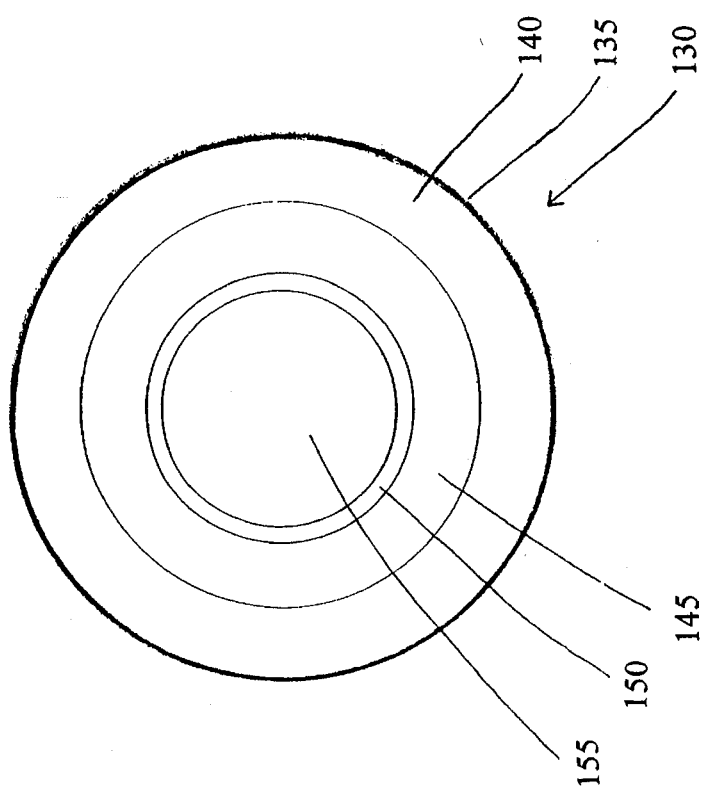
FIG. 5
FIG. 6

CATHETER FOR DELIVERING THERAPEUTIC AND/OR DIAGNOSTIC AGENTS TO THE TISSUE SURROUNDING A BODILY PASSAGEWAY

FIELD OF THE INVENTION

The present invention relates generally to catheters. More particularly, the present invention relates to an improved catheter and to a method for using the same to deliver therapeutic and/or diagnostic agents to the tissue surrounding a bodily passageway. The present invention is particularly well suited to use in connection with percutaneous transluminal angioplasty procedures, where the direct administration of drugs to the angioplasty site may help to promote improved vascular healing and to reduce restenosis.

BACKGROUND OF THE INVENTION

The use of balloon catheters to enlarge artherosclerotic blood vessels, as well as to counteract narrowing in ureters, urethras, bile ducts, fallopian tubes and the like, is well known in the art. In transluminal angioplasty, for example, a coronary artery that has become blocked with plaque (i.e., an artherosclerotic blood vessel) is enlarged through the use of a balloon catheter. This procedure has been found to be a therapeutic alternative to the surgical removal of the plaque and/or to bypass surgery.

More particularly, the balloon angioplasty procedure is generally carried out as follows. First, a balloon catheter is positioned within the restricted segment of the blood vessel. Then the catheter's balloon is inflated with a fluid (e.g. a gas or liquid) so as to compress the plaque and thereby enlarge the central lumen of the blood vessel. In this way blood flow through the vessel can be increased.

Unfortunately, such dilation of an artherosclerotic blood vessel can often cause serious damage to the blood vessel, due to the trauma associated with dilation. In particular, it has been found that the dilated blood vessel frequently has an excessive healing response, such that the blood vessel's central lumen subsequently renarrows. This frequently occurs within as little as six months after the dilation procedure is conducted.

Experimental studies have shown that administering anti-platelet, anti-coagulant, anti-proliferative and/or anti-inflammatory drugs to the site of the trauma can regulate the healing response of the tissue. Unfortunately, these drugs have traditionally been administered to the patient systemically. As a result, it has generally been necessary to administer relatively high dosages to the patient in order to achieve the desired concentrations of the drugs at the site of the trauma. These high dosage levels have sometimes caused serious side effects in the patient.

It has been recognized that the controlled delivery of these therapeutic agents directly to the trauma site would allow the desired dosages to be administered to the damaged tissue, without the occurrence of systemic toxicity. In fact, it has been found that the controlled delivery of appropriate medication directly to the trauma site is one of the most effective means of reducing the excessive healing response that causes restenosis in the dilated blood vessels.

Consequently, to avoid the dangers of systemic toxicity, various devices have been proposed to deliver medication directly to the side wall of a blood vessel.

For example, balloon catheters have been constructed where the body of the balloon is formed out of a permeable membrane. As a result, when these balloon catheters are positioned within a restricted segment of a blood vessel and their balloons subsequently inflated with an appropriate medication-containing fluid, the medication-containing fluid will pass through the wall of the balloon and into the adjacent wall of the blood vessel. In this way the desired medication can be delivered directly to the site of the angioplasty. Unfortunately, however, it has also been found that these fluid-permeable balloon catheters must generally use a relatively high fluid pressure in order to properly inflate their balloons and eject their medication-containing fluid. This pressure is at a magnitude such that it tends to cause additional damage to the wall of the blood vessel, which in turn leads to further excessive vascular healing response and hence to additional renarrowing of the blood vessel.

In another attempt to provide the local delivery of medication directly to the dilation site, encapsulated drugs have been deposited directly onto the inner wall of the blood vessel during the angioplasty procedure using a heated balloon catheter system. And in another technique, drugs have been impregnated into a hydrophilic coating which is placed on the catheter's balloon, so that the drugs are applied to the surrounding tissue during balloon inflation. Additionally, wire and/or biodegradable stents have been developed which can be impregnated with drugs so as to provide local drug delivery when those stents are deployed at the angioplasty site. Furthermore, it has also been shown that the controlled delivery of a drug to the exterior of the blood vessel by surgical techniques can help inhibit the renarrowing process (i.e., restenosis).

Unfortunately, all of the prior art devices and methods heretofore used to deliver therapeutic agents directly to the angioplasty site have suffered from one or more significant deficiencies. Until now, none have been completely effective in administering measured amounts of a therapeutic agent directly to the damaged tissue in a dilated blood vessel.

OBJECTS AND SUMMARY OF THE INVENTION

Accordingly, a primary object of the present invention is to provide an improved catheter for delivering therapeutic and/or diagnostic agents directly to the tissue surrounding a bodily passageway or other hollow structure in order to improve healing, prevent restenosis and/or aid in diagnosis. Another object of the present invention is to provide an improved catheter that comprises at least one needle cannula for delivering medication to the tissue surrounding a bodily passageway. A further object of the present invention is to provide an improved balloon catheter for use in a transluminal angioplasty procedure, wherein the catheter can be used to deliver medication directly to the dilation site at any time during the angioplasty procedure.

Another object of the present invention is to provide an improved catheter for delivering drugs directly to the tissue surrounding a bodily passageway, wherein the catheter includes means for fixedly positioning the catheter in place within the bodily passageway prior to the delivery of drugs to the surrounding tissue.

And another object of the present invention is to provide an improved method for locally administering therapeutic and/or diagnostic agents directly to the tissue surrounding a bodily passageway or other hollow structure in order to improve healing, prevent restenosis and/or aid in diagnosis.

Still another object of the present invention is to provide an improved method for locally administering medication to an angioplasty site.

These and other objects of the present invention are achieved through the provision and use of a novel catheter which is adapted to deliver therapeutic and/or diagnostic agents directly to the tissue surrounding a bodily passageway or other hollow structure.

More particularly, the novel catheter generally comprises an elongated body having a distal portion and a proximal portion, wherein the distal portion defines a distal surface; means for directing the catheter through a bodily passageway so that the distal portion of the catheter is disposed at a predetermined location within the bodily passageway; a lumen extending through the catheter's elongated body and opening on the catheter's distal surface; and a needle cannula having a distal portion and a proximal portion, wherein the distal portion of the needle cannula is adapted to pierce tissue and the proximal portion of the needle cannula is adapted to be connected to an appropriate source of therapeutic and/or diagnostic agents. The needle cannula is disposed within the lumen so that the needle cannula can be moved between (i) a first retracted position wherein the distal portion of the needle cannula is positioned within the distal portion of the catheter, just inboard of the catheter's distal surface, and (ii) a second extended position wherein the distal portion of the needle cannula is extended a predetermined distance outboard of the catheter's distal surface.

In a preferred embodiment of the present invention, the catheter further comprises a balloon fixedly and sealably secured to the distal portion of the catheter; and an inflation/deflation passageway extending through the catheter's elongated body, wherein the distal portion of the inflation/deflation passageway is in communication with the interior of the balloon, and the proximal portion of the inflation/deflation passageway is adapted to be connected to an appropriate source of inflation, whereby the balloon can be inflated or deflated on command.

The catheter is used as follows. First, the catheter's needle cannula is placed in its first retracted position. Then, with its balloon deflated, the catheter is advanced to a position within a bodily passageway so that the catheter's distal surface resides adjacent to the tissue which is to receive the desired therapeutic and/or diagnostic agents. Next, the balloon is inflated. As the balloon inflates, it engages the side wall of the bodily passageway, thereby dilating the passageway to the extent desired and fixedly positioning the catheter therein. As this occurs, the catheter's distal surface is brought into close engagement with the tissue which is to receive the therapeutic and/or diagnostic agents. With the catheter held firmly in position by the balloon, the needle cannula is advanced into its second extended position, whereby the distal portion of the needle cannula penetrates the tissue which is to receive the therapeutic and/or diagnostic agents. Then the agents are dispensed into the tissue. After the appropriate quantity of therapeutic and/or diagnostic agents have been administered to the tissue, the needle cannula is withdrawn back into its first retracted position, the balloon is deflated, and the catheter is withdrawn from the bodily passageway.

BRIEF DESCRIPTION OF THE DRAWINGS

These and other objects, features and advantages of the present invention will be more fully disclosed in, or rendered obvious by, the following detailed description of the preferred embodiments of the invention, which are to be considered together with the accompanying drawings wherein like numbers refer to like parts and further wherein:

FIG. 3 is a cross-sectional view of the catheter shown in FIG. 1, taken along line 3—3 of FIG. 1;

FIG. 4 is an enlarged side view of the proximal end of the needle cannula of the catheter shown in FIG. 1;

FIG. 5 is a schematic cross-sectional view of a healthy blood vessel;

FIG. 6 is a schematic cross-sectional view of a diseased blood vessel, particularly illustrating the build-up of plaque about the central lumen thereof;

DETAILED DESCRIPTION OF THE PREFERRED EMBODIMENTS

Figure 1:
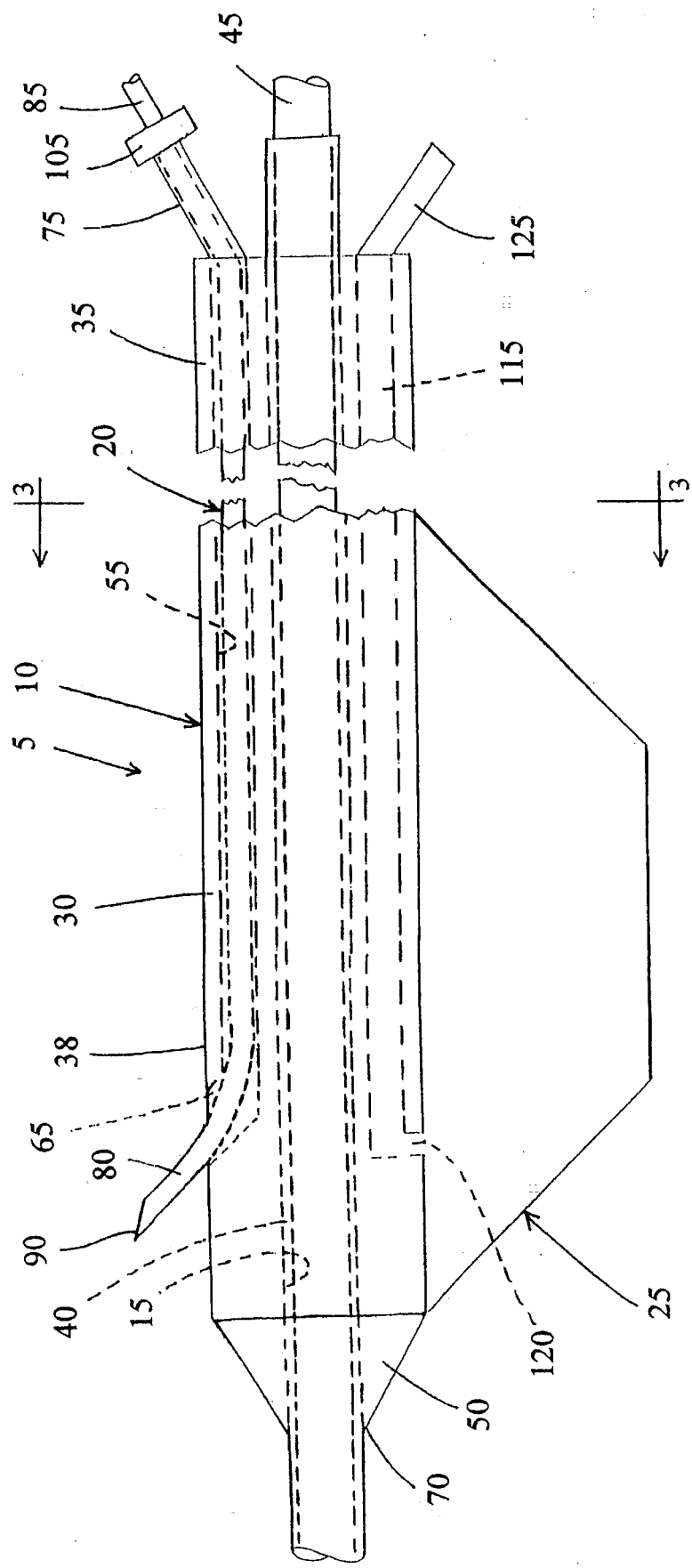
FIG. 1 is a side view of a catheter which comprises a preferred embodiment of the present invention, wherein the catheter comprises a single needle cannula and a single balloon, and further wherein the catheter's needle cannula is shown in its second extended position, and the catheter's balloon is shown fully inflated.

Looking first at FIGS. 1–4, a catheter 5 is shown which comprises a preferred embodiment of the present invention. Catheter 5 generally comprises an elongated body 10, means 15 for directing the catheter through one or more bodily passageways to a desired site, a needle cannula 20, and a balloon 25.

Elongated body 10 generally comprises a distal portion 30 and a proximal portion 35.

In the preferred embodiment of the invention, the means 15 for directing the catheter through one or more bodily passageways to a desired site generally comprise a central passageway 40 extending from distal portion 30 through proximal portion 35. Central passageway 40 is adapted to slidably accommodate a guidewire 45 extending therethrough. Guidewire 45 is of the sort commonly used to direct a catheter through one or more bodily passageways such as blood vessels. More particularly, guidewire 45 is typically formed out of a strong flexible wire such that it can be passed through various bodily passageways to reach a remote site within a patient's body. Catheter 5 can then be loaded onto guidewire 45 and passed down the guidewire until it reaches the remote site. Movement of catheter 5 through these bodily passageways is facilitated by a blunt conical nose portion 50 (FIG. 1) which is fitted onto distal portion 30.

Catheter 5 also includes a lumen 55 that extends between distal portion 30 and proximal portion 35. More particularly, lumen 55 opens on the catheter's distal surface 38 at an opening 65. Preferably, opening 65 is located approximately 1 to 3 centimeters from the distal end 70 of nose portion 50. Access to the proximal end of lumen 55 is provided via hub 75 (FIGS. 1 and 4).

Needle cannula 20 is slidably disposed in lumen 55. Needle cannula 20 comprises a distal portion 80 (FIGS. 1–3) and a proximal portion 85 (FIGS. 1 and 4). Distal portion 80 includes a tissue-piercing tip 90 (FIGS. 1 and 3) and a dispensing port 95 (FIG. 3). In the preferred embodiments of the invention, distal portion 80 is normally curved somewhat so that it will exit opening 65 at an angle of between about 30° and 90° with respect to distal surface 38. An angle of about 45° is preferred in many applications. At the same time, needle cannula 20 is formed out of a resilient material so that it can deform to the extent necessary to allow it to be retracted back into lumen 55 in the manner hereinafter discussed in greater detail.

Dispensing port 95 is in fluid communication with proximal portion 85 of needle cannula 20 via the cannula's central lumen 100 (FIG. 3). Proximal portion 85 extends through hub 75 and is adapted to be connected to dispensing means (not shown) of the sort well known in the art (e.g. a syringe or fluid pump), whereby therapeutic and/or diagnostic agents can be dispensed out of port 95 on command.

Needle cannula 20 is slidably disposed in lumen 55 so that it can move between a first retracted position (FIG. 2) and a second extended position (FIGS. 1 and 3). In its first retracted position, the needle cannula's tissue-piercing tip 90 is located inboard of the catheter's distal surface 38 so as to avoid damaging tissue during deployment of the catheter, as will hereinafter be disclosed in further detail. In its second extended position, the cannula's tissue-piercing tip 90 is located outboard of the catheter's distal surface 38 so as to permit the needle cannula's tip to penetrate the tissue defining and/or surrounding the bodily passageway in which the catheter is disposed, as will hereinafter be discussed in further detail.

As seen in FIGS. 1 and 4, the proximal portion 85 of needle cannula 20 extends out of hub 75. Proximal portion 85 includes calibrated graduations 105 (FIG. 4) positioned along its outer surface. Graduations 105 are calibrated so as to indicate the extent to which the needle cannula's tissue-piercing tip 90 extends outboard of the catheter's distal surface 38. This assists the surgeon in properly positioning tip 90 in the target tissue during use, as will hereinafter be discussed in further detail. A stop 110 is provided to limit the distal movement of needle cannula 20 relative to catheter body 10 and, therefore, to limit the extent to which tissue-piercing tip 90 can penetrate into any tissue located adjacent to the catheter.

Figure 2:
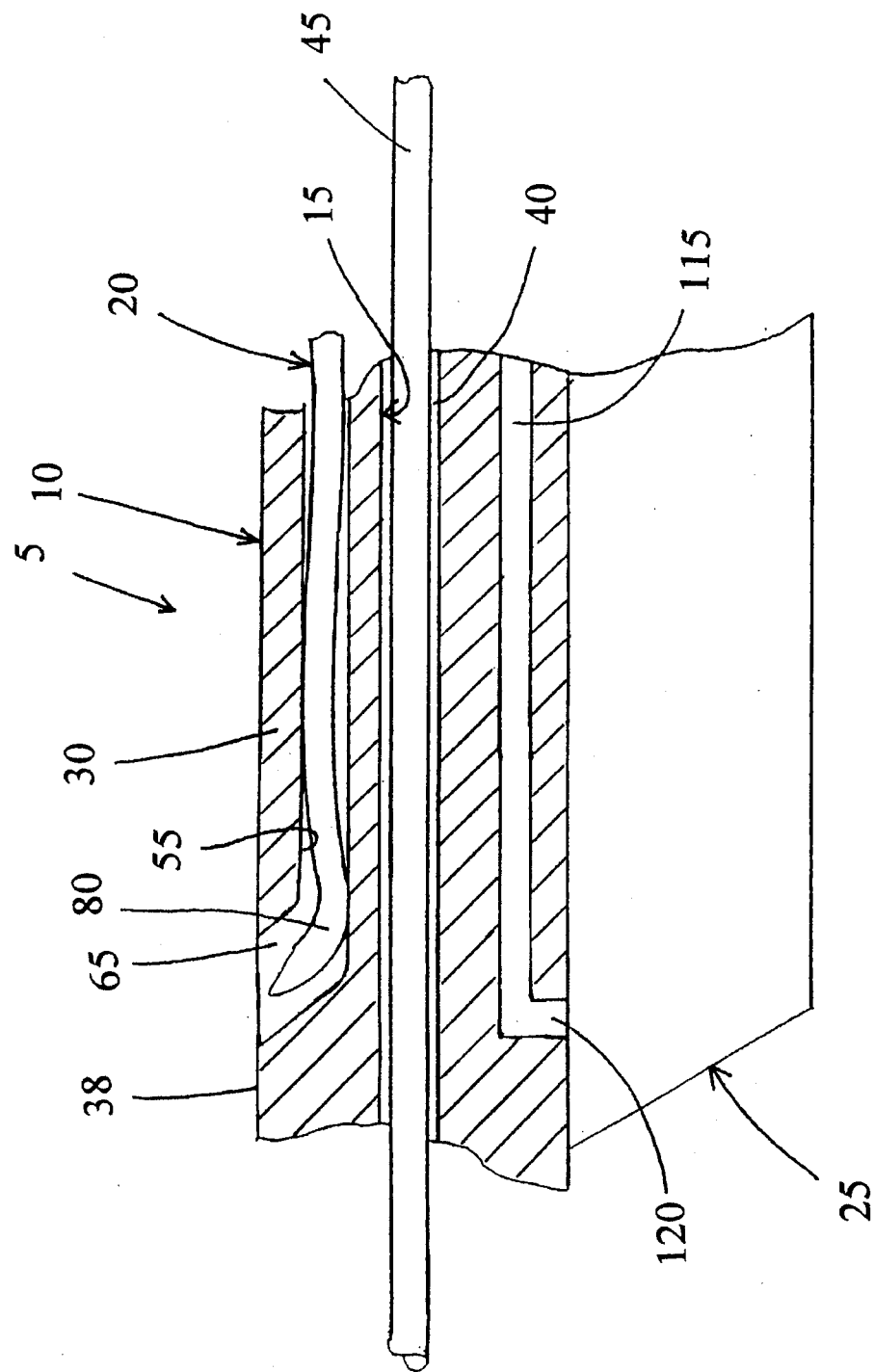
FIG. 2 is a partial side view, in partial section, of the catheter shown in FIG. 1, wherein the catheter's needle cannula is shown in its first retracted position.

Looking now at FIGS. 1–3, catheter 5 also comprises the balloon 25. Balloon 25 is fixedly and sealably secured to the catheter's distal portion 30. Balloon 25 extends both longitudinally and circumferentially about at least a part of distal portion 30.

An inflation/deflation passageway 115 (FIGS. 1–3) extends from the catheter's distal portion 30 to its proximal portion 35. Inflation/deflation passageway 115 includes an opening 120 (FIGS. 1 and 2) located within distal portion 30 that communicates with the interior of balloon 25. Inflation/deflation passageway 115 extends along the length of the catheter, from opening 120 in distal portion 30, through distal portion 30, and through proximal portion 35. Inflation/deflation passageway 115 exits shaft 10 through a hub 125 (FIG. 1). Hub 125 is adapted to be connected to appropriate inflation means (not shown) of the sort well known to those skilled in the art, whereby balloon 25 can be inflated or deflated on command.

It will be appreciated that balloon 25 may be inflated by the introduction of either gases or liquids into inflation/deflation passageway 115. It will also be appreciated that liquids containing therapeutic and/or diagnostic agents may also be used to inflate balloon 25, and that balloon 25 may be made of a material that is permeable to such therapeutic and/or diagnostic liquids, whereby such liquids may be ejected into adjacent bodily tissues during balloon inflation. In any event, balloon 25 is generally constructed so that it may be inflated to between 15 and 30 psi during use. In the preferred embodiment of the present invention, balloon 25 comprises an inelastic material.

As previously discussed, transluminal angioplasty is a technique which is frequently used to enlarge a blood vessel, such as a coronary artery, that has become occluded by the build-up of plaque. The use of the foregoing catheter 5 will now be discussed in the context of performing such a procedure.

More particularly, and looking now at FIG. 5, a typical healthy coronary artery 130 is shown. Artery 130 generally comprises an outside artery wall 135, a layer of adventitial tissue 140, the media 145, and the intima 150. These tissue structures are arranged in substantially concentric layers about a central lumen 155. Contrastingly, in an artherosclerotic coronary artery 160 such as that illustrated in FIG. 6, the central lumen 165 has been significantly reduced in diameter due to the build-up of plaque on the intima 170.

Catheter 5 can be used to reopen the narrowed central lumen 165 of artery 160. This is done as follows. First, a guidewire 45 is introduced into the arterial system of the patient at an appropriate location, e.g., the femoral artery. Then the guidewire is snaked through the patient's arteries until the distal end of guidewire reaches the narrowed central lumen 165 of artery 160. Next the catheter 5 is mounted on the proximal end of the guidewire 45 and slid down the guidewire until it is positioned in the narrowed central lumen 165 of artery 160, in the manner shown in FIG. 7.

During the foregoing catheter insertion procedure, balloon 25 is in its deflated state, and needle cannula 20 is disposed in its first retracted position so that its tissue-piercing tip 90 is located just inboard of distal surface 38 (FIG. 2). This allows the catheter to pass smoothly through the patient's arteries without damaging the surrounding tissue or impeding the movement of the catheter.

Once catheter 5 has been properly positioned within the reduced diameter lumen 165 of diseased coronary artery 160, balloon 25 is inflated. This causes catheter 5 to engage and compact the plaque built up on the artery's intima 170, in the manner shown in FIG. 9. As a result, the artery's central lumen 165 is dilated. Of course, since balloon 30 is asymetrically disposed about the distal portion 30 of catheter 5, at least some blood will continue to flow around the catheter even when the balloon 25 is fully inflated within the artery.

Figure 8:
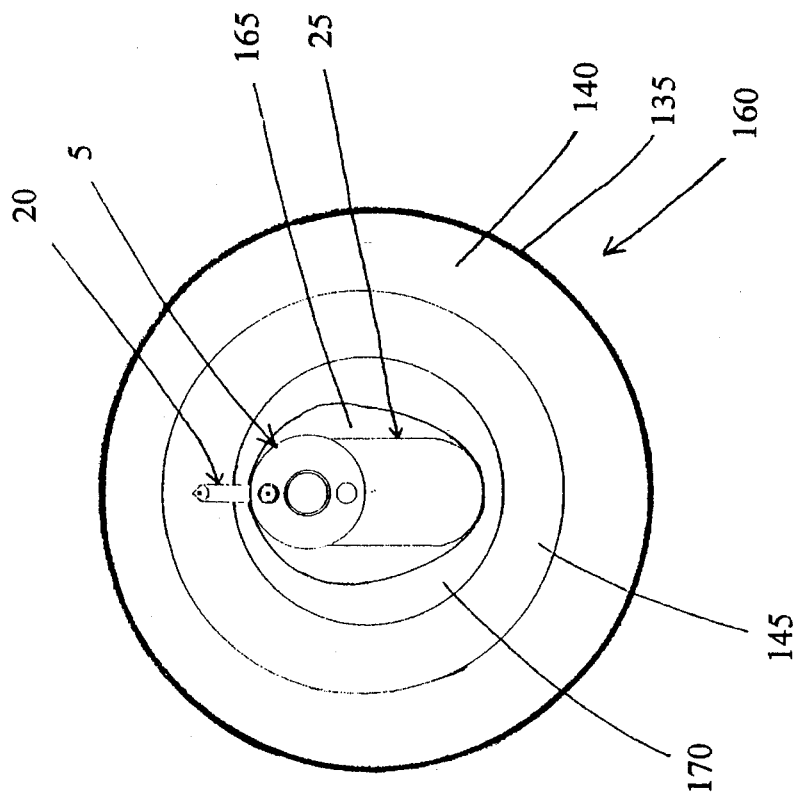
FIG. 8 is a view similar to that of FIG. 7, except that the catheter's balloon has been inflated so as to dilate the blood vessel, and the catheter's needle cannula has been advanced into its second extended position so as to penetrate the tissue surrounding the vessel's central lumen.

It will be appreciated that catheter 5 will be securely fixed in position in artery 160 when balloon 25 is fully inflated, with the plaque compacted and with the artery's central lumen 165 dilated. At the same time, the catheter's distal surface 38 will have been brought into direct engagement with intima 170. At this point the surgeon may slide needle cannula 20 distally within lumen 55, by pushing the needle cannula's proximal portion 35 distally into hub 75, so that needle cannula 20 will move from its first retracted position (FIG. 2) to its second extended position (FIGS. 1, 3 and 8). As this occurs, the needle cannula's tissue-piercing tip 90 will penetrate to the adjacent tissue. The surgeon may regulate the degree of penetration by observing the calibrated graduations 105 which are disposed on the proximal portion 85 of needle cannula 20.

Figure 7:
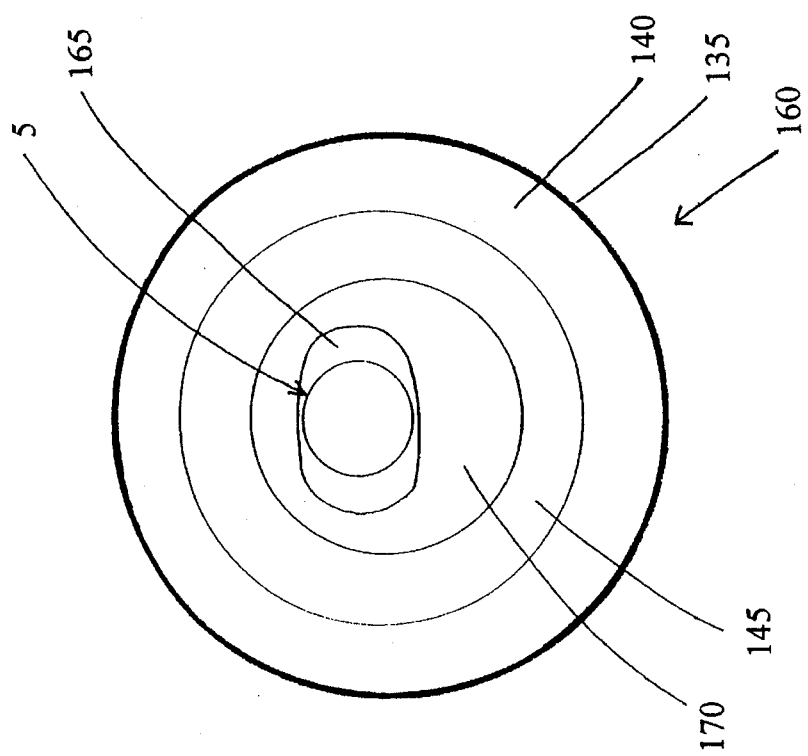
FIG. 7 is a view similar to that of FIG. 6, except that the catheter of FIG. 1 has been positioned within the central lumen of the partially blocked blood vessel, with the catheter's needle cannula being in its first retracted position, and with the catheter's balloon being in its deflated state.

Advantageously, needle cannula 20 may be extended so as to position its dispensing port 95 in any one of the concentric tissue layers 140, 145 and/or 170 disclosed in FIGS. 6–8, and/or outside of those tissue layers and into the surrounding tissues and/or organs. It is to be appreciated that as needle cannula 20 is extended out of catheter 5 in this manner, the catheter will be held securely in position within the artery by its inflated balloon 25. Once the catheter's tissue-piercing tip 90 has been properly positioned within the surrounding tissue, the surgeon may proceed to dispense a measured quantity of therapeutic and/or diagnostic agents into that tissue.

Once the desired therapeutic and/or diagnostic agents have been administered to the surrounding tissue, needle cannula 20 is withdrawn from its second extended position (FIGS. 1, 3 and 8) into its first retracted position (FIG. 2). Then balloon 30 is deflated and catheter 5 withdrawn from the patient's body in ways well known in the art.

The catheter 5 described above constitutes a preferred embodiment of the present invention. As noted previously, it comprises a single needle cannula 20 and a single balloon 25. It is to be appreciated, however, that various modification may be made to the foregoing catheter 5 without departing from the scope of the present invention.

For example, during some surgical procedures it may be necessary or desirable to deliver more than one type of therapeutic and/or diagnostic agent to the same tissue, or to deliver the same therapeutic and/or diagnostic agent to more than one location in the tissue. Accordingly, a catheter may be provided which comprises more than one needle cannula. More particularly, and looking now at FIGS. 9 and 10, a catheter 175 is shown which comprises two needle cannulas 20A and 20B which are positioned within two lumens 55A and 55B. Needle cannulas 20A and 20B are substantially identical to the needle cannula 20 disclosed in FIGS. 1–4, and lumens 55A and 55B are substantially identical to the lumen 55 disclosed in FIG. 1–4. More particularly, needle cannula 20A comprises a distal portion 80A, a tissue-piercing tip 90A, a dispensing port 95A, and a central lumen 100A, all substantially identical to the corresponding structures disclosed previously in connection with needle cannula 20. Needle cannula 20B similarly comprises a distal portion 80B, a tissue-piercing tip 90B, a dispensing port 95B (not shown in FIGS. 9 and 10, but shown in FIG. 11) and a central lumen 100B, all also substantially identical to the corresponding structures previously disclosed in connection with needle cannula 20.

Figure 10:
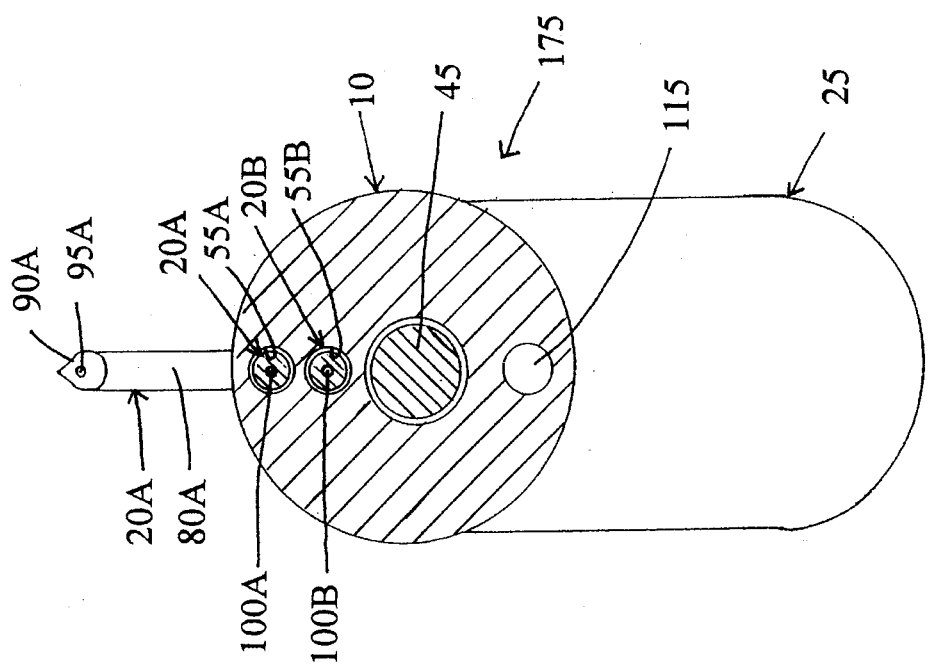
FIG. 10 is a cross-sectional view of the catheter shown in FIG. 9, taken along line 10—10 of FIG. 9.

The two needle cannulas 20A and 20B are positioned one above the other in catheter body 10, as shown in FIG. 10. It will be appreciated that needle cannulas 20A and 20B may or may not be operated independently of each other, as preferred, but in any case they are each operated in substantially the same manner as previously disclosed in connection with the discussion of needle cannula 20 shown in FIGS. 1–4. In this way, more than one therapeutic and/or diagnostic agent may be delivered to the same tissue, or the same therapeutic and/or diagnostic agent may be to more than one location in the tissue, either to different depths or into different tissue, as required.

Figure 9:
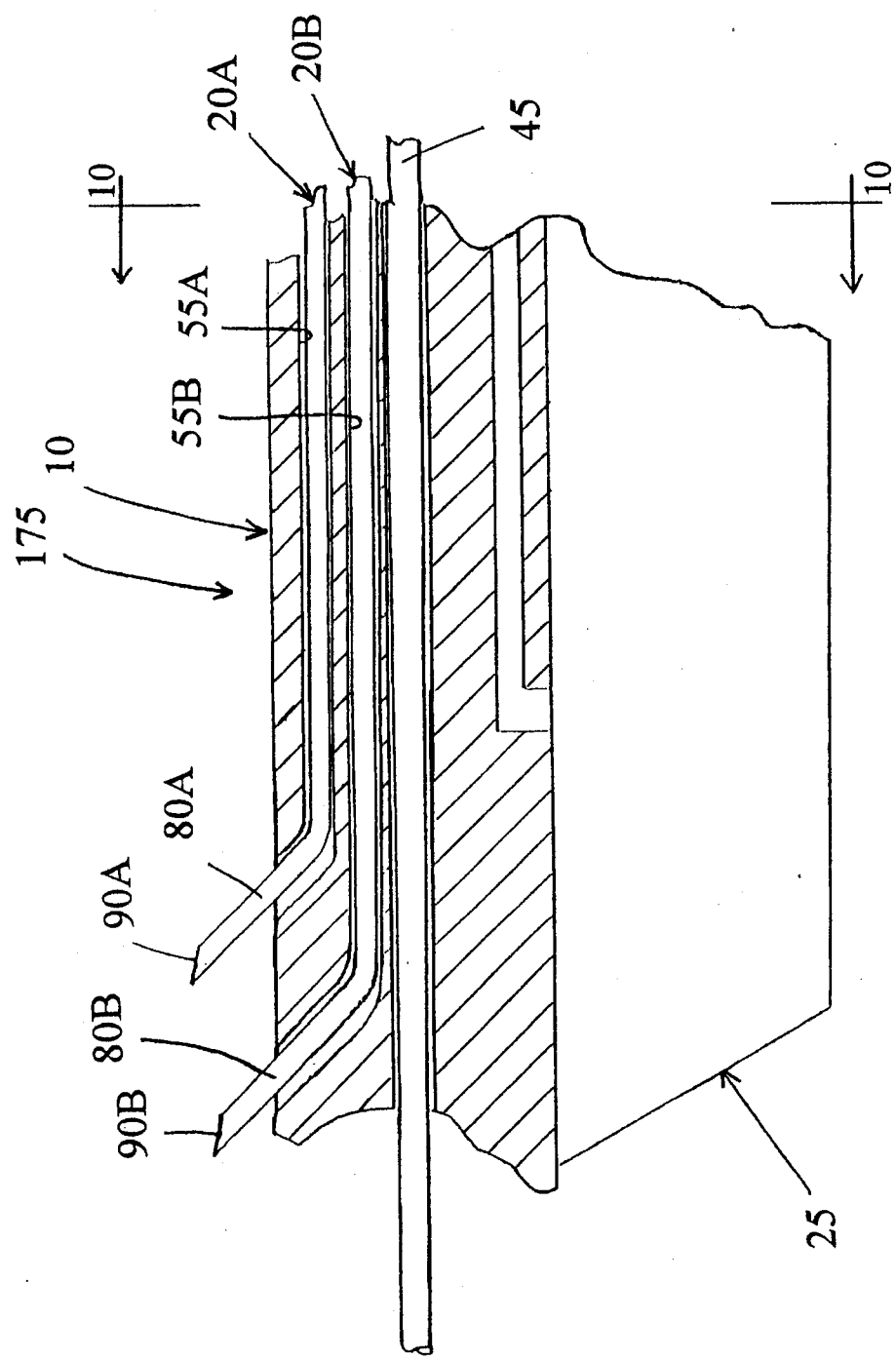
FIG. 9 is a partial side view, in partial section, of a catheter which comprises an alternative embodiment of the present invention, wherein the catheter comprises a pair of needle cannulas and a single balloon, and further wherein the two needle cannulas are both shown in their second extended position, and the catheter's balloon is shown in its inflated state.
Figure 11:
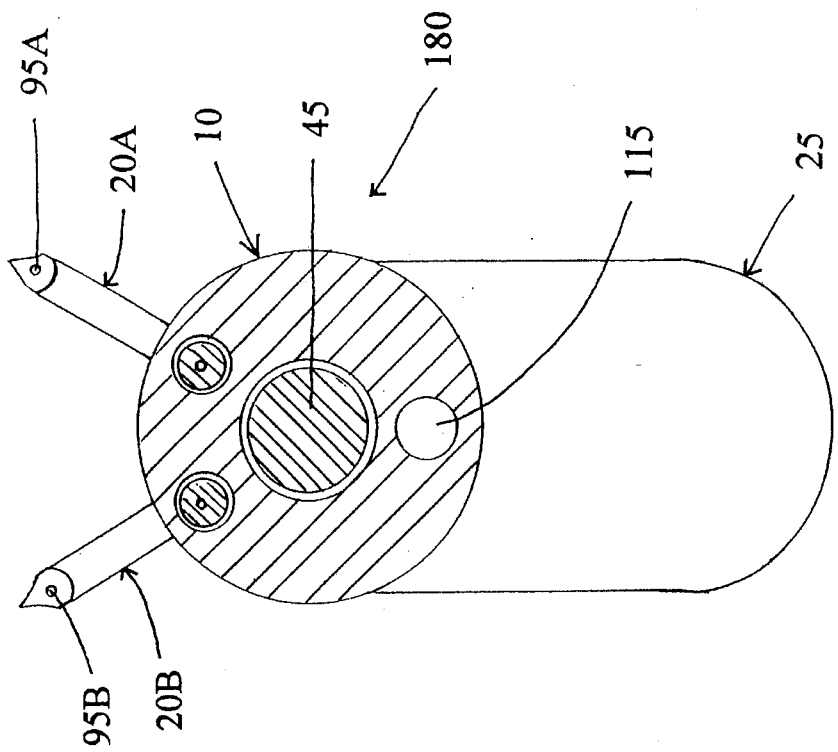
FIG. 11 is a cross-sectional view similar to that of FIG. 10, but illustrating a further alternative embodiment of the present invention wherein the two needle cannulas are positioned in circumferentially-spaced relationship to one another.

Needle cannulas 20A and 20B may be disposed within the catheter's elongated body 10 in some relationship other than the stacked, radially-spaced arrangement shown in FIGS. 9 and 10. For example, FIG. 11 shows a catheter 180 in which needle cannulas 20A and 20B are placed side-by-side, in a circumferentially-spaced relationship, rather than stacked in a radially-spaced relationship. Again, needle cannulas 20A and 20B may or may not be operated independently of each other, as preferred, but in any case they are each operated in substantially the same manner as previously disclosed in connection with the discussion of needle cannula 20 shown in FIGS. 1–4.

Figure 12:
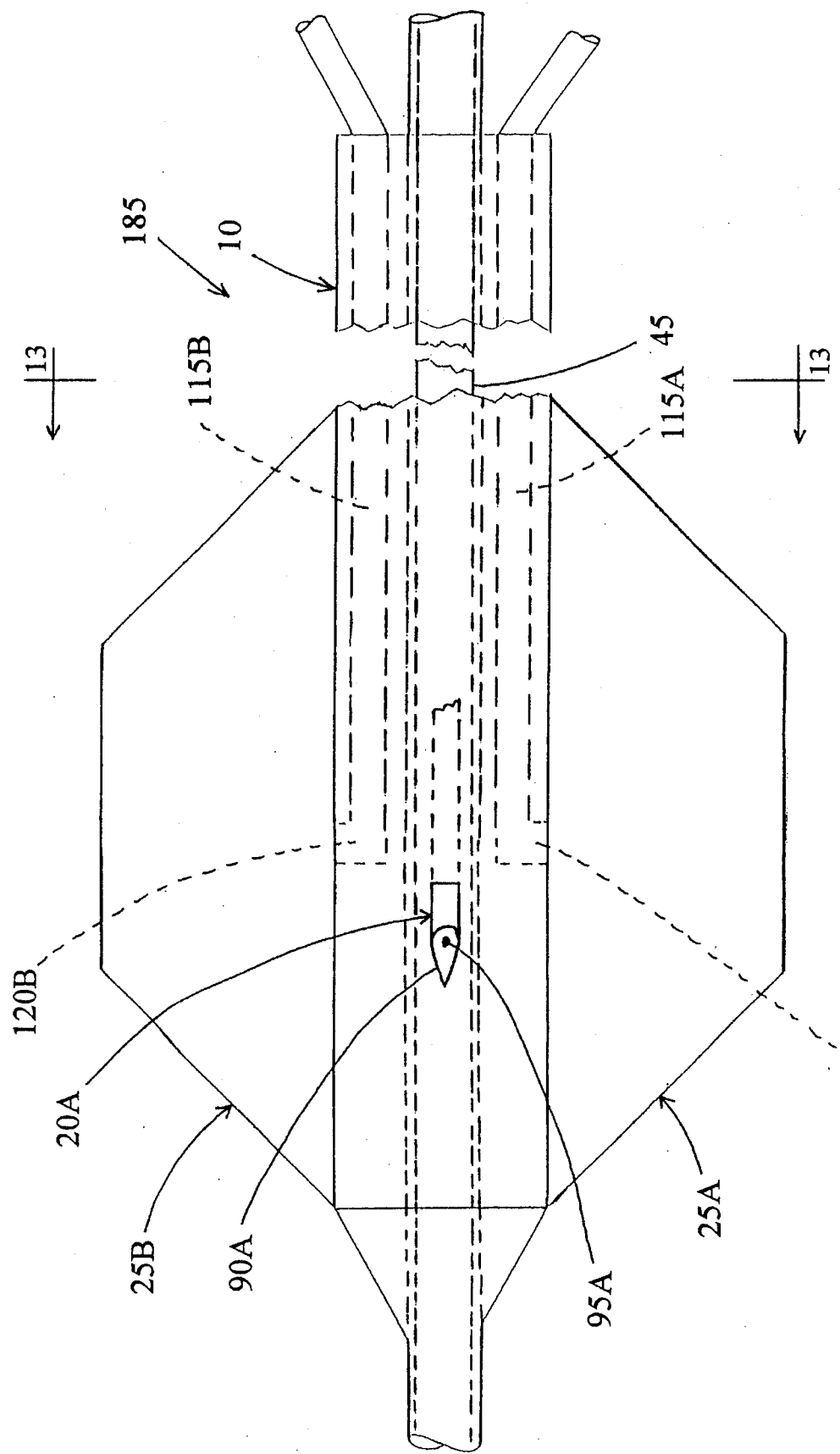
FIG. 12 is a side view of a catheter which comprises still another alternative embodiment of the present invention, wherein the catheter comprises a pair of needle cannulas and a pair of balloons, and further wherein one of the needle cannulas is shown in its second extended position and both of the catheter's balloons are shown in their inflated state.
Figure 13:
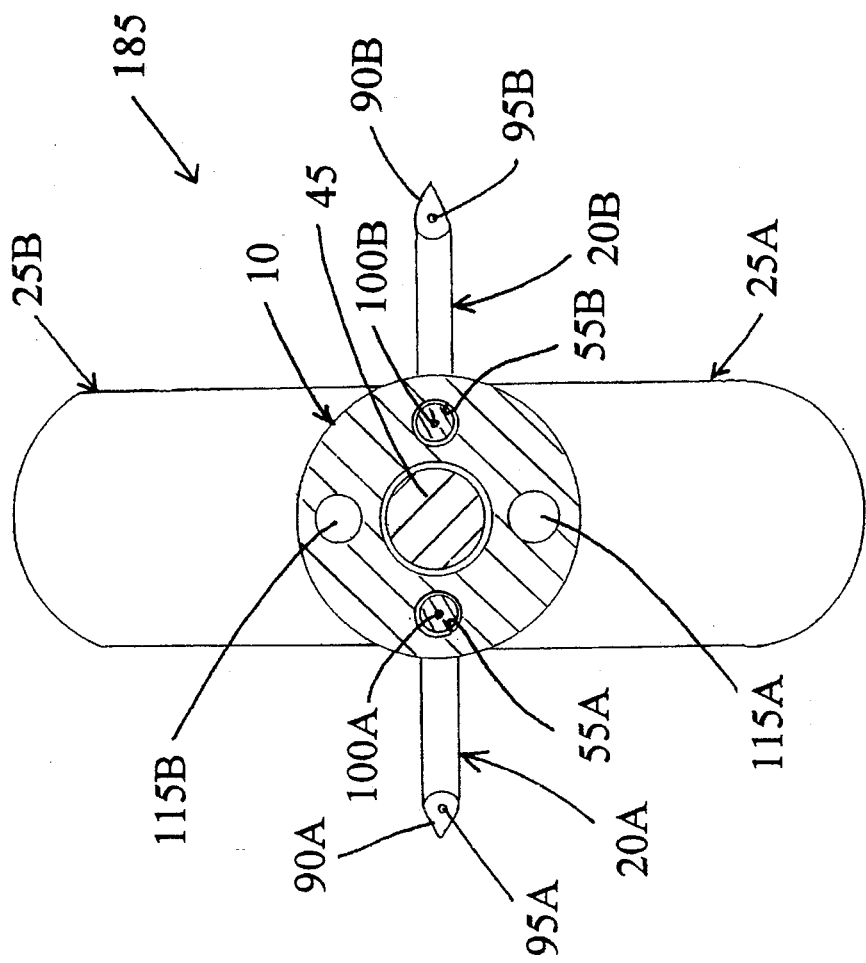
FIG. 13 is a cross-sectional view of the catheter shown in FIG. 12, taken along line 13—13 of FIG. 12.

It will also be appreciated that more than one balloon may be disposed about the distal portion of the catheter. More particularly, and looking now at FIGS. 12 and 13, a catheter 185 is shown which comprises two needle cannulas 20A and 20B and two balloons 25A and 25B. Needle cannulas 20A and 20B are disposed in diametrically-opposed, equally-circumferentially-spaced relationship to one another (FIG. 13). Similarly, balloons 25A and 25B are disposed in diametrically-opposed, equally-circumferentially-spaced relationship to one another (FIGS. 12 and 13).

Needle cannulas 20A and 20B are substantially identical to the needle cannula 20 disclosed in FIGS. 1–4. More particularly, needle cannulas 20A and 20B are slidingly positioned within lumens 55A and 55B, respectively, which extend through catheter body 10. Needle cannulas 20A and 20B include tissue-piercing tips 90A and 90B, respectively. Dispensing ports 95A and 95B are disposed in their respective tissue-piercing tips 90A and 90B, and communicate with central lumens 100A and 100B, respectively. Needle cannulas 20A and 20B may or may not be operated independently of one another, as preferred, but in any case they are each operated in substantially the same manner as the needle cannula 20 disclosed in connection with FIGS. 1–4.

Balloons 25A and 25B are substantially identical to the balloon 25 disclosed in FIGS. 1–4. More particularly, balloons 25A and 25B are disposed about the distal portion of catheter body 10 and communicate with inflation/deflation passageways 115A and 115B, respectively, via openings 120A and 120B, respectively. Balloons 25A and 25B may or may not be operated independently of one another, as preferred, but in any case they are each operated in substantially the same manner as the balloon 25 disclosed in connection with FIGS. 1–4.

Thus it will be seen that with this embodiment of the present invention, the surgeon may inject therapeutic and/or diagnostics agents at diametrically-opposed, equally-circumferentially-spaced locations around the bodily passageway, while the catheter is held in place within the passageway with a pair of diametrically-opposed balloons.

Figure 14:
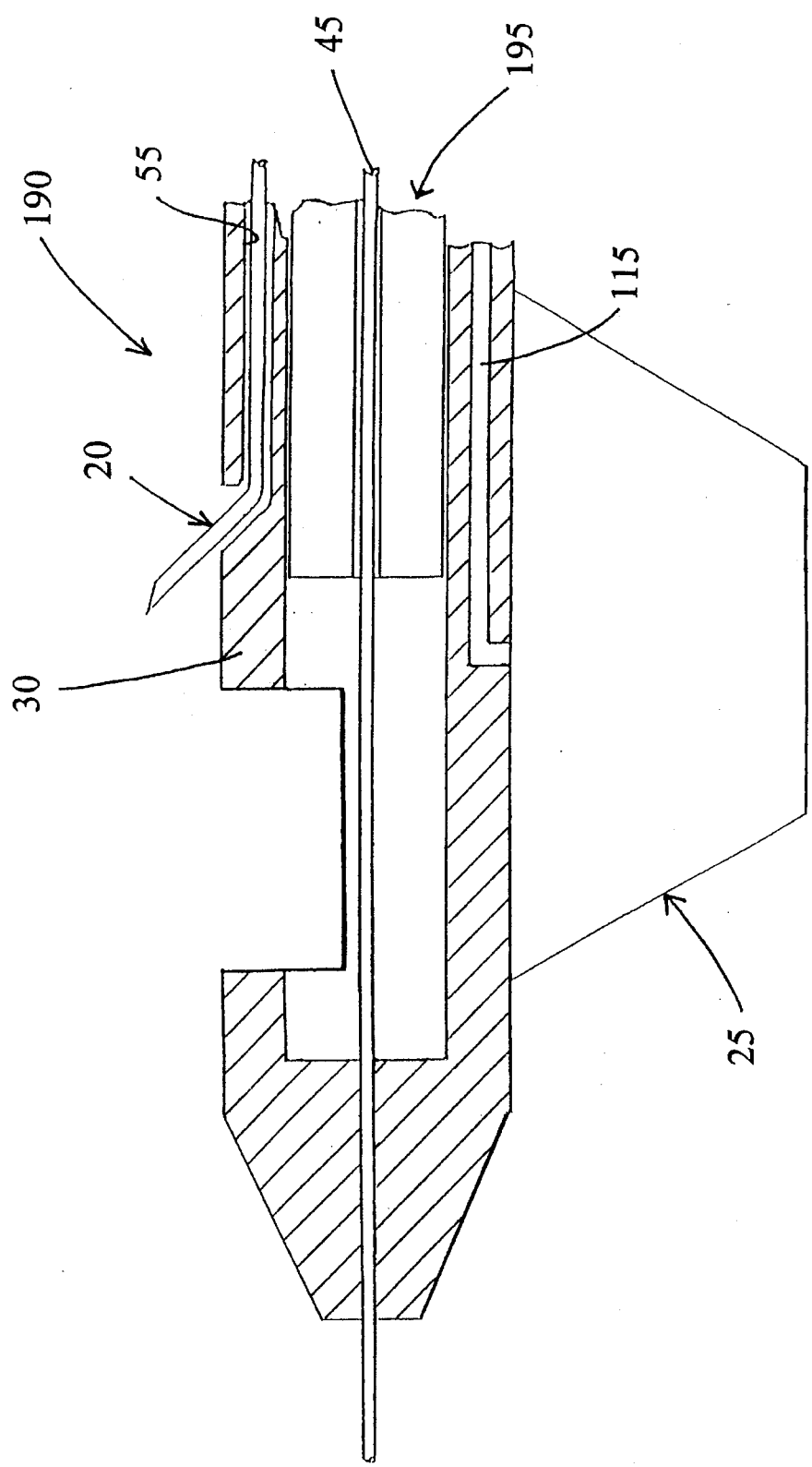
FIG. 14 is a side view of a catheter which comprises yet another alternative embodiment of the present invention, wherein the catheter comprises a single needle cannula and a single balloon, and wherein the catheter's needle cannula is shown in its second extended position and the catheter's balloon is shown fully inflated, and further wherein the catheter comprises tissue cutting means.

It is sometimes necessary to use a catheter to sever and remove tissue from a bodily passageway, e.g. a blood vessel. In such a case, it may also be desirable to locally deliver therapeutic and/or diagnostic agents to the surrounding tissue at the same time that severing and removal is being effected. To this end, and referring now to FIG. 14, a catheter 190 is shown which has tissue cutting and removal means 195 located in the distal portion 30 of the catheter. Tissue cutting and removal means 195 might comprise a Simpson arthrectomy device such as that marketed by Devices For Vascular Intervention Inc. (DVI) of Redwood many tissue cutting and removal devices of the sort well known in the art, as preferred. Catheter 190 includes a needle cannula 20 (shown in its second extended second position) and a balloon 25 (shown fully inflated). Needle cannula 20 and balloon 25 are substantially identical to the corresponding structures shown in FIGS. 1–4 and operate in a substantially identical manner. Catheter 190 is disposed within a bodily passageway in the same manner as has been previously disclosed in connection with the catheter 5 shown in FIGS. 1–4. In this case, however, cutting means 195 may also be used in ways well known in the art to sever and remove tissue from the bodily passageway.

Figure 15:
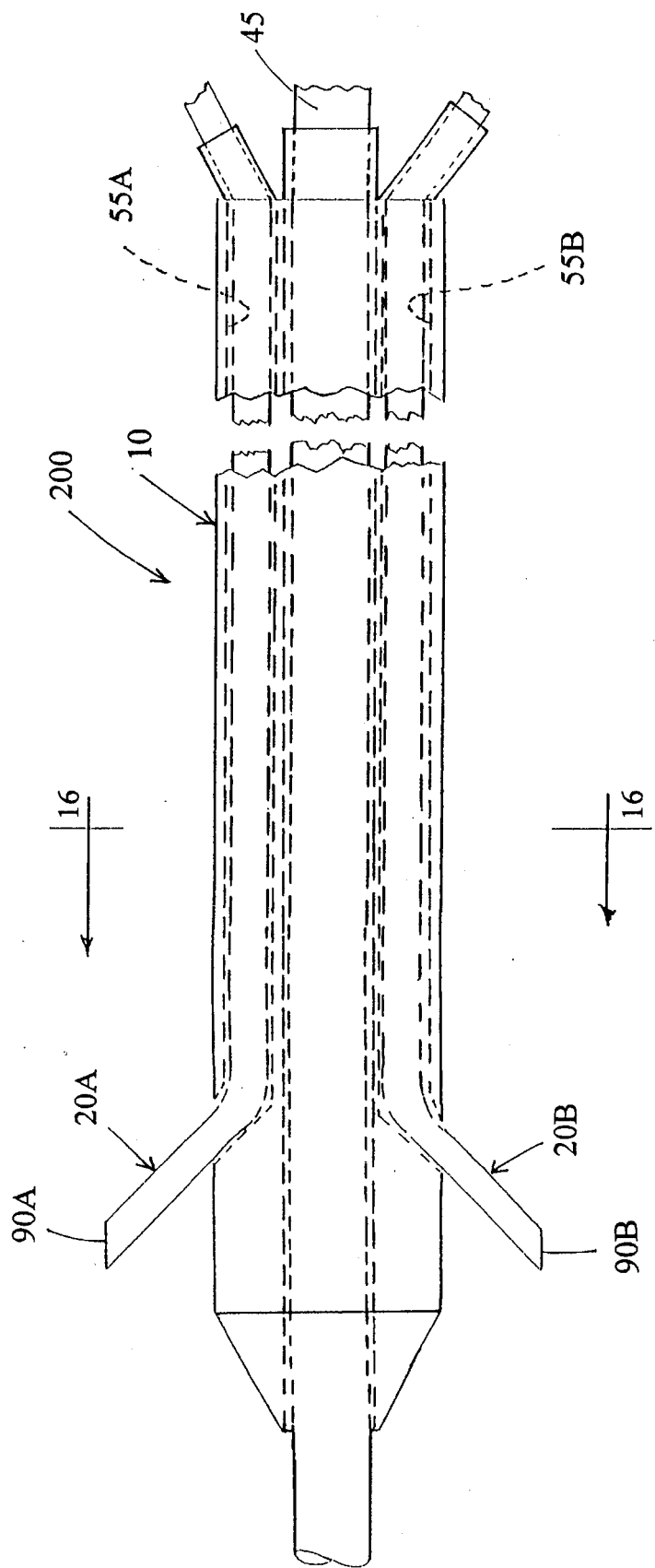
FIG. 15 is a side view of a catheter which comprises still another embodiment of the present invention, wherein the catheter comprises a pair of needle cannulas and no balloon, and further wherein the catheter's needle cannulas are both shown in their second extended position.

The catheter of the present invention may also be provided with one or more needle cannulas as indicated above but omit the provision of a balloon. More particularly, and looking now at FIGS. 15 and 16, a catheter 200 is shown which comprises two needle cannulas 20A and 20B. Needle cannulas 20A and 20B are substantially identical to the needle cannula 20 shown in FIGS. 1–4. More particularly, needle cannulas 20A and 20B are slidably positioned in lumens 55A and 55B, respectively, which extend through catheter body 10. Needle cannulas 20A and 20B include tissue-piercing tips 90A and 90B, respectively. Dispensing ports 95A and 95B are disposed in their respective tissue-piercing tips 90A and 90B, and communicate with central lumens 100A and 100B, respectively. Needle cannulas 20A and 20B may or may not be operated independently of one another, as preferred, but in any case they are each operated in substantially the same manner as the needle cannula 20 previously disclosed in connection with FIGS. 1–4.

Similar embodiments having 1, 3, 4 or more needle cannulas are also considered to be within the scope of the present invention.

Figure 16:
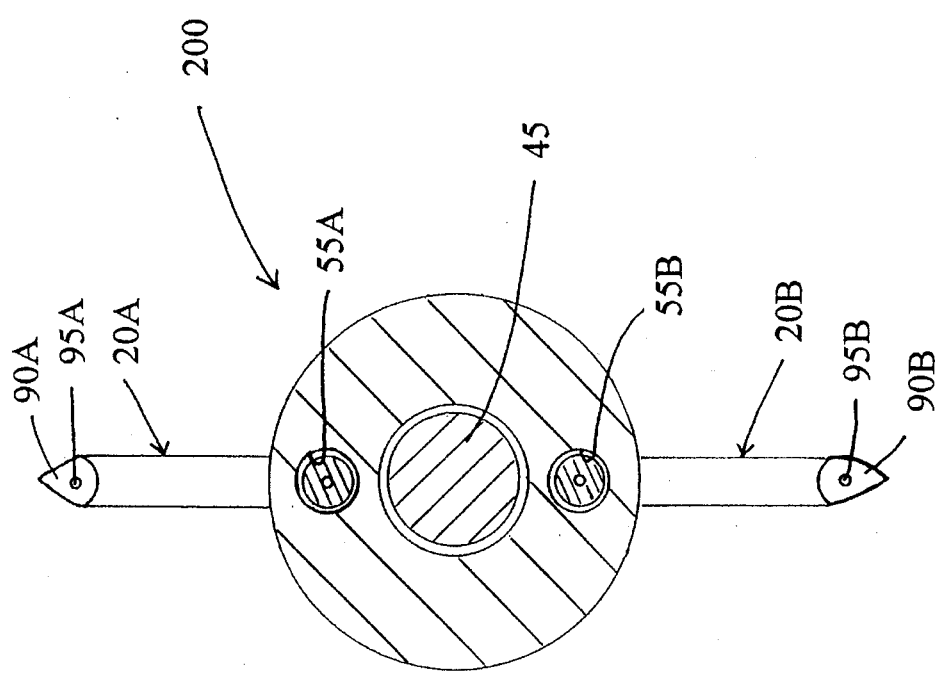
FIG. 16 is a cross-sectional view of the catheter shown in FIG. 15, taken along line 16—16 of FIG. 15.

Needle cannulas 20A and 20B may extend outwardly in diametrically-opposed, equally-circumferentially-spaced relationship to one another as seen in FIG. 16, or they may be positioned about the circumference of the catheter in a manner similar to that depicted in FIGS. 10, 11, or 13. Advantageously, the needle cannulas 20A and 20B are deployed in substantially the same manner as previously disclosed in connection with the needle cannula 20 of FIGS. 1–4, except that needle cannulas 20A and 20B now provide the additional benefit of collectively anchoring the catheter 200 in place within a bodily passageway.

Figure 17:
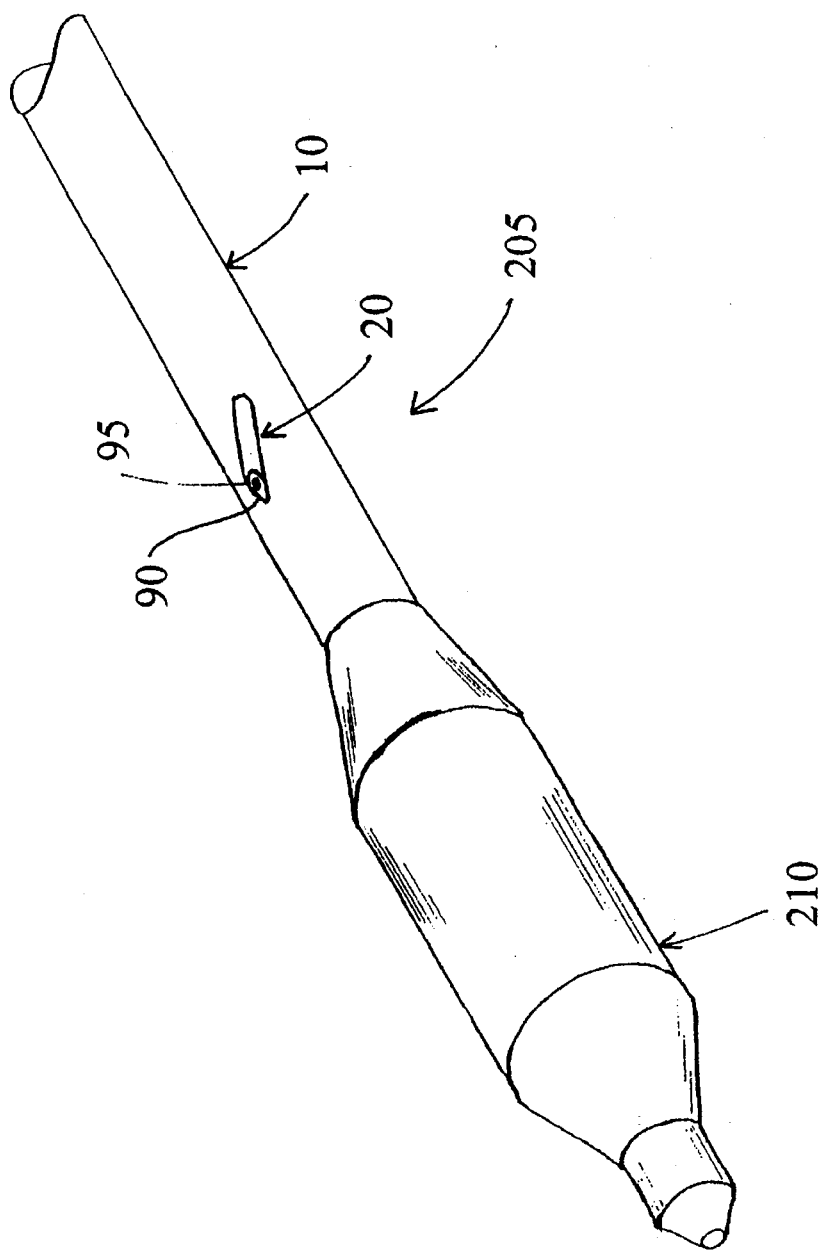
FIG. 17 is a perspective view of a catheter which comprises yet another embodiment of the present invention, wherein the catheter comprises a single needle cannula and a single balloon, wherein the catheter's balloon extends completely around the distal portion of the catheter, and the needle cannula is adapted to exit the catheter on the proximal side of the balloon, and further wherein the needle cannula is shown in its second extended position and the balloon is shown fully inflated.
Figure 18:
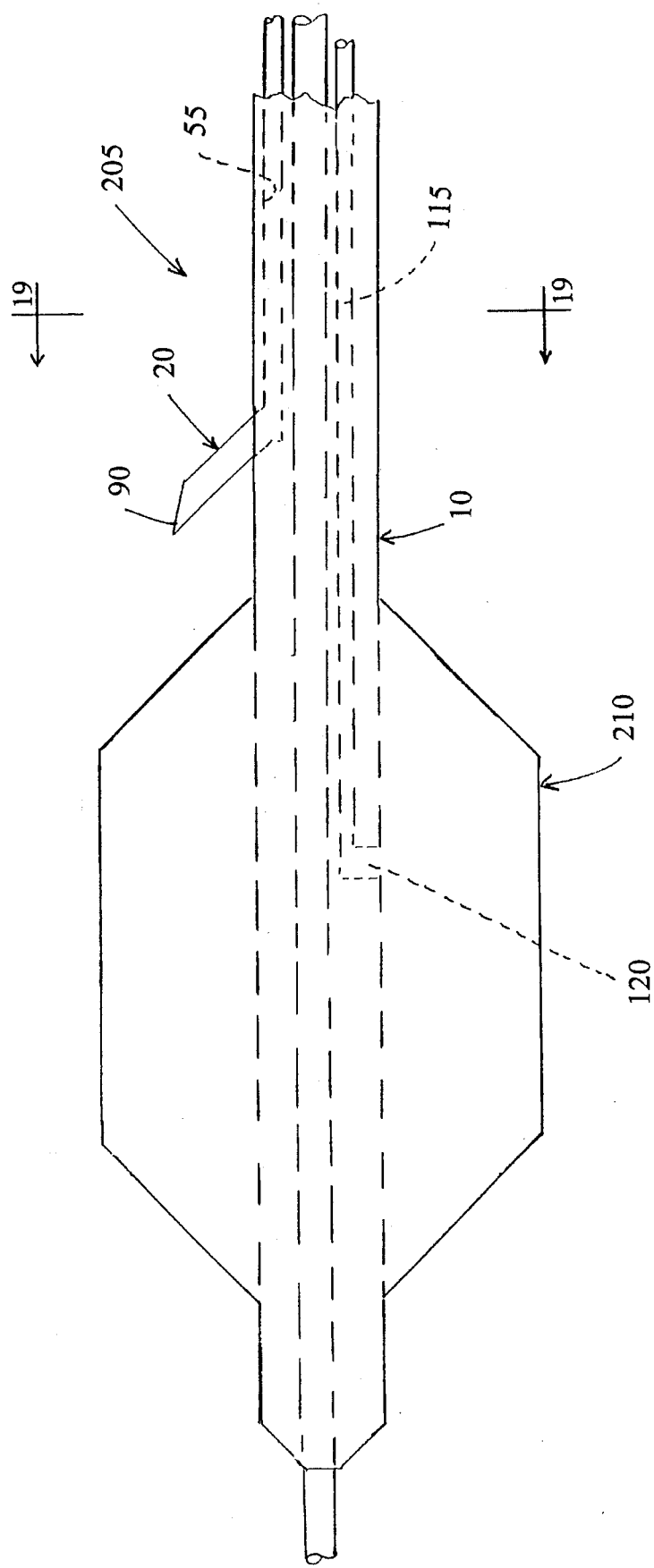
FIG. 18 is a side view of the catheter shown in FIG. 17.
Figure 19:
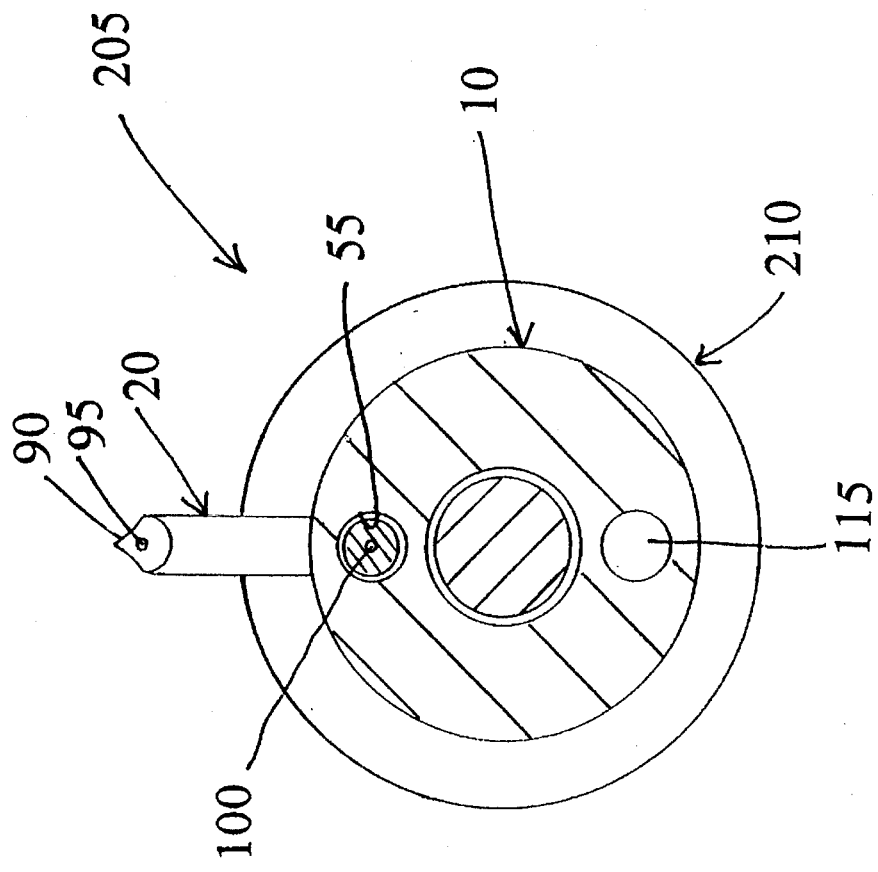
FIG. 19 is a cross-sectional view of the catheter shown in FIGS. 17 and 18, taken along line 19—19 FIG. 18.

It is also to be appreciated that the new catheter may utilize a balloon having a configuration different than the balloon 25 shown in FIGS. 1–4. More particularly, and referring now to FIGS. 17–19, a catheter 205 is shown which comprises a needle cannula 20 and a balloon 210.

Needle cannula 20 is substantially identical to the needle cannula 20 disclosed in FIGS. 1–4. More particularly, needle cannula 20 is slidingly positioned within lumen 55 which extends through body 10. Needle cannula 20 includes a tissue-piercing tip 90 and a dispensing port 95 which communicates with central lumen 100. Needle cannula 20 is operated in substantially the same manner as the needle cannula 20 disclosed in FIGS. 1–4.

Balloon 210 is disposed circumferentially about the entire circumference of the distal portion of catheter 210. An inflation/deflation passageway 115 extends through catheter body 10 and communicates with the interior of balloon 210 through an opening 120, whereby balloon 210 may be inflated or deflated on command.

Still other variations, modifications, alterations, changes, uses, and the like will occur to those skilled in the art in light of the foregoing description of the preferred embodiment of the invention. For example, the present invention may be used in those instances requiring fixed positioning of medication dispensing means within a bodily passageway other than blood vessels, e.g., ureters, urethras, bile ducts, fallopian tubes and the like.

What is claimed is:

1. A catheter for delivering therapeutic and/or diagnostic agents directly into tissue surrounding a bodily passageway, comprising:

an elongated body having a distal portion and a proximal portion, said distal portion including a distal surface;

means for directing said elongated body through said bodily passageway so that said distal portion is positioned at a predetermined location therein;

first and second lumens communicating between said distal surface and said proximal portion of said elongated body, said first lumen communicating with said distal surface through a needle exit opening disposed therein;

a needle cannula slidably disposed in said first lumen, said needle cannula comprising a distal portion and a proximal portion, said proximal portion being adapted to be connected to means for dispensing said therapeutic and/or diagnostic agents;

said needle cannula being adapted for movement between (i) a first retracted position wherein said distal portion of said needle cannula is withdrawn inboard of said distal surface, and (ii) a second extended position wherein said distal portion of said needle cannula extends a predetermined distance outboard of said distal surface; and a balloon fixedly and sealably secured to said distal portion of said elongated body and in fluid communication with said second lumen for dilating said bodily passageway when said balloon is inflated and compacting plaque that has been deposited in said passageway, said balloon extending both longitudinally and circumferentially along only a side portion of said distal portion of said catheter so as to be in opposing radial alignment with said needle exit opening such that when said balloon is fully inflated (i) fluid flow is not restricted through said bodily passageway, and (ii) said needle cannula may be extended said predetermined distance into said tissue surrounding said bodily passageway at a predetermined location.

2. A catheter according to claim 1 wherein said catheter comprises at least two lumens and at least two needle cannulas, wherein each of said needle cannulas is slidably disposed in one of said lumens.

3. A catheter according to claim 2 wherein said at least two lumens are radially aligned with one another.

4. A catheter according to claim 2 wherein said at least two lumens are circumferentially spaced from one another.

5. A catheter according to claim 1 wherein said catheter comprises at least two balloons and at least two inflation/deflation passageways, wherein each of said inflation/deflation passageways is in communication with the interior of one of said balloons.

6. A catheter according to claim 5 wherein said at least two balloons are circumferentially spaced from one another.

7. A catheter according to claim 6 wherein said catheter comprises at least two lumens and at least two needle cannulas, wherein each of said needle cannulas is slidably disposed in one of said lumens, and further wherein said lumens are circumferentially spaced from one another.

8. A catheter according to claim 1 further comprising tissue severing means disposed on a portion of said elongated body.

9. A method for delivering therapeutic and/or diagnostic agents directly into tissue surrounding a bodily passageway, said method comprising the steps of:

(1) providing a catheter comprising:
    an elongated body having a distal portion and a proximal portion, said distal portion including a distal surface;
    means for directing said elongated body through said bodily passageway so that said distal portion is positioned at a predetermined location therein;
    a first lumen communicating between said distal surface and said proximal portion of said elongated body, said first lumen communicating with said distal surface through a needle exit opening disposed therein;
    a needle cannula slidably disposed in said first lumen, said needle cannula comprising a distal portion and a proximal portion, said proximal portion being adapted to be connected to means for dispensing said therapeutic and/or diagnostic agents;
    said needle cannula being adapted for movement between (i) a first retracted position wherein said distal portion of said needle cannula is withdrawn inboard of said distal surface, and (ii) a second extended position wherein said distal portion of said needle cannula extends a predetermined distance outboard of said distal surface; and
    a balloon fixedly and sealably secured to said distal portion of said elongated body and in fluid communication with an inflation/deflation lumen for dialating said bodily passageway and compacting plaque that has been deposited therein, said balloon extending both longitudinally and circumferentially along only a side portion of said distal portion of said catheter so as to be in opposing radial alignment with said needle exit opening such that when said balloon is fully inflated (i) fluid flow is not restricted through said bodily passageway, and (ii) said needle cannula may be extended said predetermined distance into said tissue surrounding said bodily passageway at a predetermined location;

(2) positioning said needle cannula in its said first retracted position and placing said balloon in its deflated state;

(3) positioning said catheter in said predetermined location in said bodily passageway;

(4) inflating said balloon so as to fixedly position said catheter within said bodily passageway;

(5) moving said needle cannula from said first fully retracted position to said second extended position, whereby a distal end of said needle cannula penetrates tissue surrounding said bodily passageway;

(6) dispensing said therapeutic and/or diagnostic agents from said distal end of said needle cannula;

(7) moving said needle cannula from said second extended position back into said first retracted position;

(8) deflating said balloon; and (9) removing said catheter from said bodily passageway.

10. A catheter according to claim 1 wherein said needle cannula comprises a curved distal portion adapted to project outwardly from said needle exit opening, when said needle cannula is in said second extended position, at an angle of between about 30 degrees and about 90 degrees with respect to said distal surface of said elongated body.

11. A catheter according to claim 10 wherein said angle is about 45 degrees.

12. A catheter according to claim 1 wherein said balloon comprises a material that is permeable to liquids containing said therapeutic and/or diagnostic agents, whereby such liquids may be ejected into adjacent bodily tissues during inflation of said balloon.

13. A catheter according to claim 1 wherein said balloon comprises an inelastic material.

14. A catheter according to claim 1 wherein said balloon is asymetrically disposed about said distal portion of said elongated body.

15. A catheter according to claim 1 wherein said proximal portion of said needle cannula comprises a plurality of calibrated graduations whereby the degree of penetration of said needle cannula into said tissue surrounding said bodily passageway may be determined.

16. A catheter according to claim 1 wherein said means for directing said elongated body through said bodily passageway comprise a guidewire adapted for insertion into and travel through said bodily passageway.

* * * * *